United States Patent [19]

Lörincz et al.

[11] 4,334,910
[45] Jun. 15, 1982

[54] PLANT-PROTECTIVE AND PEST-CONTROL AGENT

[75] Inventors: Csaba Lörincz; Éva Lörincz neé Csapó; István Gebhardt; Antal Gimesi; Béla Stefko; Erik Bogsch; Zsuzsanna Földesi neé Szász; Kálmán Szász, all of Budapest, Hungary

[73] Assignee: Richter Gedeon Vegyészeti Gyár Rt., Budapest, Hungary

[21] Appl. No.: 718,990

[22] Filed: Aug. 30, 1976

[30] Foreign Application Priority Data

Sep. 1, 1975 [HU] Hungary ............................. RI 576
Sep. 1, 1975 [HU] Hungary ............................. RI 578

[51] Int. Cl.³ .............................................. A01N 59/02
[52] U.S. Cl. ..................................... 71/82; 71/80; 71/83; 71/84; 71/DIG. 1; 71/65; 71/93; 71/121
[58] Field of Search ............................... 71/82, 93, 65

[56] References Cited

U.S. PATENT DOCUMENTS 1,925,628  9/1933  Chipman ............................ 71/84
3,492,110  1/1970  Hood et al. ........................ 71/93
3,634,062  1/1972  Berrer et al. ...................... 71/93
3,957,481  5/1976  Bollinger et al. .................. 71/93

FOREIGN PATENT DOCUMENTS 1502307  11/1966  France ............................. 71/93
4011633   6/1965  Japan .............................. 71/65

OTHER PUBLICATIONS

Galloway, "Pesticides", 1962, CA 58, p. 9576, (1963).
Aliev, "The Use of 2,4-d for Weed Control in Corn", (1959), CA 54, p. 25490, (1960).

*Primary Examiner*—Glennon H. Hollrah
*Attorney, Agent, or Firm*—Karl F. Ross

[57] ABSTRACT

A herbicidal composition capable of preventing weed growth of potatoes or soybean plants consists of a triazene or an aromatic nitro compound together with an inorganic salt, especially sodium bisulfate or potassium bisulfate which reduced the quantity of the organic herbicide below that usually required to obtain a corresponding herbicidal effect and hence prevents phytotoxic damage. The composition contains 0.1:1 to 15:1 parts by weight of the inorganic compound to the organic compound and is applied in an amount of 0.1 to 30 kg of the composition per hectare.

14 Claims, No Drawings

PLANT-PROTECTIVE AND PEST-CONTROL AGENT

This invention relates to plant-protective and pesticidal agent with herbicidal, insecticidal and fungicidal effectiveness as well as its use in agriculture, including horticulture.

In the following the term "pesticide" as used in the Anglo-Saxon literature will be employed instead of the expression "Plant-Protective and Pest-Control Agent", and will be understood in the description to include herbicidally, fungicidally or insecticidally effective agents.

The use of chemicals in agriculture is, apart from beneficial, also a source of several hazards, for example, environmental pollution, since, for example, the soil treated with the chemicals may become contaminated to the detriment of useful organisms living in the soil, and, on the other hand, may render free water (e.g. rivers and lakes) unsatisfactory as a fish habitat when certain agricultural chemicals are transferred thereto by rainwater or sprinkling water. Moreover, the known herbicides in many cases used for crops are too phytotoxic. Consequently it is essential to reduce the applied amount of pesticidally effective organic compounds to achieve a given pesticidal effect to the absolute minimum.

The invention has the object of obviating the disadvantages of the state of the art by providing new superior pesticides that are substantially less and generally not poisonous and phytotoxic.

It has been found surprisingly that, by the mixing of known pesticidally effective organic compounds with one or more of the salts sodium and/or potassium and/or bisulphate and/or bisulphite and/or dithionite and/or sulphate and by using such mixtures as pesticides, the poisonousness of and phytotoxicity of the pesticidally effective organic compounds is reduced and in many cases completely eliminated because a signficant amount of these compounds, which would otherwise be required, is substituted by nonpoisonous and nonphytotoxic easily available inorganic salts, whereby the pesticidal effect of such mixtures is increased in a synergistic manner to at least the same pesticidal effect as in the case of the use of an identical quantity of the pesticidally effective organic substances alone.

The subject of the invention is thus a pesticide which is characterized by containing, together with one or more of the salts sodium and/or potassium bisulphate, bisulphite, dithionite, and/or sulphate, one or more pesticidally effective organic compounds as effective agents, advantageously together with carrier substances, extenders, diluting agents and/or auxiliary substances.

The invention thus has very great technical advantages in that the pesticide according to the invention is of better or at least equal pesticidal effectiveness to the known pesticide alone but has a significantly reduced poisonousness and phytotoxicity with respect to plant cultures. They therefore can be used on plant cultures to a greater extent since there is a significant increase in tolerance. The phytotoxic damage to plant cultures, which accompanies the use of the pesticidally effective organic compounds themselves, is substantially reduced since the pesticides according to the invention have substantially reduced amounts of pesticidally effective compounds than is the case when these compounds alone are used as the effective material. The use of the pesticidal mixtures according to the invention is substantially more economical than when organic compounds made only by complicated techniques in multistage synthesis are used alone as the effective material, because the pesticidal mixtures according to the invention utilize, in place of a part of these compounds, commercially available inorganic salts and nevertheless obtain a pesticidal effect by pesticides prepared by simple mixing which is better or at least as great as that obtained with the same amount of the previously used pesticidal compound alone.

Preferably the pesticide according to the invention uses as the pesticidally effective component effective compounds, one or more asymmetric and/or symmetric triazine derivatives.

The chemical names of the compounds are the first ones listed in "Pesticide Manual" (H. Martin and Ch. R. Worthing; British Crop Protection Council, 4th edition, 1974). The common names of these compounds accepted or suggested by the ISO (International Organization for Standardization), BSI (British Standards Institution) or WSSA (Weed Science Society of America) are given in brackets.

The triazine derivatives in the pesticides according to the invention are, for example, the following:
2-ethylamino-4-isopropylamino-6-methylthio-1,3,5-triazine (Ametryne),
2-chloro-4-ethylamino-6-isopropylamino-1,3,5-triazine (Atrazine),
2-azido-4-isopropylamino-6-methylthio-1,3,5-triazine (Aziprotryne),
2-chloro-4-(1'-cyano-1'-methylethylamino)-6-ethylamino-1,3,5-triazine (Cyanazine),
2-chloro-4-cyclopropylamino-6-isopropylamino-1,3,5-triazine (Cyprazine),
2-isopropylamino-4-methylamino-6-methylthio-1,3,5-triazine (Desmetryne),
2-(1',2'-dimethylpropylamino)-4-ethylamino-6-methylthio-1,3,5-triazine (Dimethametryn),
2-ethylthio-4,6-di(isopropylamino)-1,3,5-triazine (Dipropetryn),
2-isopropylamino-4-(3-methoxypropylamino)-6-methylthio-1,3,5-triazine (Methoprotryne),
4-amino-6-tert-butyl-4,5-dihydro-3-methylthio-1,2,4-triazine-5-one (Metribuzin),
2,4-di(isopropylamino)-6-methoxy-1,3,5-triazine (Prometron),
2,4-di(isopropylamino)-6-methylthio-1,3,5-triazine (Prometryne),
2-chloro-4,6-di(isopropylamino)-1,3,5-triazine (Propazine),
2-sec-butylamino-4-ethylamino-6-methoxy-1,3,5-triazine (Secbumeton),
2-chloro-4,6-di(ethylamino)-1,3,5-triazine (Simazine),
2-tert-butylamino-4-ethylamino-6-methoxy-1,3,5-triazine (Terbumeton),
2-tert-butylamino-4-chloro-6-ethylamino-1,3,5-triazine (Terbuthylazine),
2-tert-butylamino-4-ethylamino-6-methylthio-1,3,5-triazine (Terbutryne), and
2-chloro-4-diethylamino-6-ethylamino-1,3,5-triazine (Trietazine).

The following especially preferred triazine derivatives are the following:
2-chloro-4-ethylamino-6-isopropylamino-1,3,5-triazine (Atrazine), 2-chloro-4-(1'-cyano-1'-methylethylamino)-6-ethylamino-1,3,5-triazine (Cyanazine), 2-chloro-4-cyclopropylamino-6-isopropylamino-1,3,5-triazine (Cyprazine), 2-ethylamino-4-isopropylamino-6-methylthio-1,3,5-triazine (Ametryne), 2,4-di(isopropylamino)-6-methylthio-1,3,5-triazine (Prometryne), 4-amino-6-tert-butyl-4,5-dihydro-3-methylthio-1,2,4-triazine-5-one (Metribuzin), 2-chloro-4,6-di(isopropylamino)-1,3,5-triazine (Propazine), and 2-tert-butylamino-4-ethylamino-6-methylthio-1,3,5-triazine (Tertbutryne).

In the pesticides according to the invention, the following examples of aromatic nitro compounds are given:

N-n-butyl-N-ethyl-2,6-dinitro-4-trifluoromethylaniline (Benefluralin), 3,5-dibromo-4-hydroxy-benzaldehyde-2',4'-dinitrophenyloxime (Bromofenoxim), 4-(2',4'-dichlorophenoxy)-2-methoxy-1-nitrobenzene (2,4-dichlorophenyl-3-methoxy-4-nitrophenyl ether), $N^1,N^1$-diethyl-2,6-dinitro-4-trifluoromethyl-m-phenylenediamine (Dinitramine), 2-sec-butyl-4,6-dinitrophenyl-isopropyl carbonate (Dinobuton), 4-nitrophenyl-2'-nitro-4'-trifluoromethylphenyl ether (Fluorodifen), 4-isopropyl-2,6-dinitro-N,N-dipropylaniline (Isopropalin), 4-methylsulfonyl-2,6-dinitro-N,N-dipropylaniline (Nitralin), 2,4-dichlorophenyl-4'-nitrophenyl ether (Nitrofen), 3,5-dinitro-$N^4,N^4$-dipropylsulfanilamide (Oryzalin), and 2,6-dinitro-N,N-dipropyl-4-trifluoromethylaniline (Trifluralin).

Especially preferred aromatic nitro compounds are the following:

N-n-butyl-N-ethyl-2,6-dinitro-4-trifluoromethylaniline, 4-isopropyl-2,6-dinitro-N,N-dipropylaniline, and 2,6-dinitro-N,N-dipropyl-4-trifluoromethylaniline.

The pesticides according to the invention are, however, not limited in their content to the above-named organic effective substances given by way of example or their combinations, but can include any pesticidally effective organic compounds and combinations of the same.

Preferably the amount of the effective material (content of the effective mixture) of the pesticides according to the invention is 0.01 to 98 weight percent.

The pesticide according to the invention can contain the inorganic salt and the pesticidally effective organic compounds or their mixtures, in very wide ranges of weight proportion. The proportion of the inorganic salt to the pesticidally effective organic compounds amounts preferably to 0.1:1 to 15:1.

The invention relates also to the use of the pesticide according to the invention or their effective mixtures, in the treatment of plants or their parts, seeds or soil, whereby they can possibly be formed upon the latter.

Furthermore, the invention relates to the use of one or more of the salts sodium and/or potassium bisulphate, bisulphite, dithionite and/or sulphate to improve the characteristics of pesticides, especially by reducing the poisonousness and phytotoxicity with reference to plant cultures and a multiple increase in the pesticidal effectiveness.

The mixture of inorganic salts and pesticidally effective organic compounds (hereinafter effective mixtures) can, preferably after being formed into preparations, be used in agriculture including gardening as plant protective agents.

The mixtures of inorganic salts and pesticidally effective organic compounds can be worked up into preparations in ways known per se. In these preparations, the pesticidally effective mixture can be mixed with carrier materials, extenders, diluents and/or other auxiliary substances.

The carrier substances, extenders or diluents can advantageously be usual inert solid and/or liquid materials and/or inert gases.

As the auxiliary agents there are the following preferably:

surface active agents, especially wetting, emulsifying and/or dispersing agents, anti-adhesion agents, lubricants, bonding agents or adhesion-increasing agents, coloring agents, corrosion inhibitors, suspending agents, and agents promoting penetration by or for increasing the resistance towards rain.

The pesticides according to the invention can include with advantages as further auxiliaries other biologically active substances and/or substances for preserving, increasing or modifying the biological activity.

Examples of suitable solid carriers or extenders are: inactive mineral substances, such as aluminum silicate, talc, calcined magnesium oxide, silicic earth, tricalcium phosphate, carbon black, powdered cork, clays, e.g. kaoline, bentonite, montmorillonite, diatomaceous earth and attapulgite, calcium phosphate, calcium carbonate, mica, pyrophillite, dolomite, gypsum, colloidal silica, Fuller's earth and Hewitt's earth.

Suitable liquid carriers and extenders are generally e.g. aqueous or water and as required water-diluted organic solvents, for example, ketones such as acetone, cyclohexanone and isophorone, aromatic hydrocarbons such as benzene, toluene, xylene, alkylnaphthalenes and tetrahydronaphthalene, chlorinated hydrocarbons, such as chlorobenzenes, dichloroethane, trichloroethylene and tetrachloroethane, alcohols, such as methanol, butanol, isopropanol, propylene glycol and diacetonealcohol, kerosene, oils of mineral, vegetable and animal origin, aliphatic mineral oil fractions, high boiling aromatic petroleum distillates such as naphtha and distilled tar oil, polar organic solvents such as dimethyl formamide, dimethyl sulfoxide and mixtures thereof.

Examples of inert gases suitable as carriers are freon-type gases and various chlorinated or fluorinated methane and ethane derivatives, such as fluorodichloromethane and difluorodichloromethane.

The wetting, dispersing and emulsifying agents can be ionic or non-ionic surface active substances.

Examples of suitable non-ionic surface-active substances are condensation products of ethylene oxide formed with fatty alcohols with 10 to 20 carbon atoms, such as oleyl alcohol, cetyl alcohol and octadecyl alcohol or with alkylphenols such as octylphenol, nonylphenol and octylcresol, or with amines such as oleylamine, or with mercaptans such as dodecyl mercaptan or with carboxylic acids as well as the partial esters of long-chain fatty acids with hexitanhydrides, the condensation products of ethylene oxide with these esters or hexitanhydrides, lecethine, and fatty acid esters of polyalcohols.

The ionic surfactant can be cationically or anionically active.

Examples of suitable anionic surfactants are the soaps, salts of aliphatic sulfuric acid monoesters such as sodium laurylsulfate, the sodium salt of sulfuric acid dodecylester, salts of sulfonated aromatic compounds such as sodium dodecylbenzenesulfonate, sodium, calcium or ammonium ligninsulfonate, butylnaphthalenesulfonate, and mixtures of sodium diisopropyl- and triisopropylnaphthalenesulfonates, the sodium salts of petroleum sulfonic acids and the potassium or triethanolamine salts of oleic acid and abietic acid.

Suitable cationically active substances are for example the quaternary ammonium compounds, such as cetyltrimethylammonium bromide, cetylpyridinium bromide and dioxoethylbenzyldodecyl ammonium bromide.

Examples of suitable suspending agents as hydrophilic colloids, such as polyvinylpyrrolidone, sodium carboxymethylcellulose, as well as vegetable gums, such as gum acacia and tragacanth.

Examples of suitable adhesion or adhesion-increasing agents are lubricants, such as calcium and magnesium stearate as well as further adhesives, such as polyvinyl alcohol, cellulose derivatives and other colloidal substances, for example, caseine and mineral oils.

Examples of suitable dispersing agents are methyl cellulose, ligninsulfonates and alkylnaphthalenesulfonates.

Examples of additives which resist or promote penetration by rain are fatty acids, resins, glue, caseine or alginates.

Optionally the pesticides according to the invention can contain protecting agents in an amount of 0.0001 to 30 percent by weight calculated on the active mixture; the protecting agents and the pesticidally effective mixture can be applied, however, separately as well, by, for example, applying the protecting agent onto the seeds and applying the pesticide to the soil either before or after sowing.

The effective mixtures according to the invention can be prepared together with the named carriers, extenders, diluents and/or auxiliary substances as various solid, liquid or gaseous preparations for use in agriculture including horticulture. Depending upon the different use requirements various suitable preparations can be readied.

The solid preparations may preferably be powders, particularly wettable and/or dispersible powders (spray powders), pellets, granules or pastes.

The liquid preparations can preferably be solutions especially directly usable, or sprayable solutions, and indeed aqueous solutions as well as solutions in organic solvents including the oil and miscable oils as well as, further, dispersions or suspensions, especially aqueous suspensions, aqueous or oily emulsions or inverted emulsions.

The gaseous preparations can preferably be aerosols.

The powdery compositions can be prepared for example in the manner that the effective mixture according to the invention is intimately mixed with one or more of the above-mentioned inert solid carriers.

The wettable or dispersible powders can be prepared in the manner that the effective mixture according to the invention is mixed with one or more of the above-mentioned inert solid carriers and moreover with one or more of the above-mentioned wetting or dispersing agents.

Pellet or granular preparations can be prepared by dissolving active mixtures according to the invention in a solvent and applying the solution in the presence of a binder onto the surface of a granular carrier, such as porous particles, e.g. of pumice stone or attapulgite corresponding to a zeolite (Attaclay) consisting of magnesium aluminum silicate, non-porous mineral granules, for example, sand or loamy soil, or an organic granular substance, for example, black soil or cut tobacco stems, and, if necessary, dried. Furthermore, pelletized, respectively, granular preparations also can be prepared in the manner that active mixtures according to the invention are mixed with powdered mineral substances in the presence of a binding agent and a lubricant, the obtained pressed body is comminuted and is sifted to the desired grain fraction. According to a preferred variant of preparing pelletized or granular preparations are the dry or wet pelletizing or granulation techniques. In the latter case the wet pelletizing or granulation as well as build-up pelletizing or granulation can be used.

Aqueous solutions, dispersions, suspensions or emulsions can be prepared in such manner that the active mixture according to the invention is dissolved in one or more solvents, whereby the solvent optionally contains one or more wetting, dispersing, suspending or emulsifying agents. The obtained mixture is diluted with water, which may also contain one or more wetting, dispersing, suspending or emulsifying agents, if necessary.

The directly sprayable preparations can be prepared in such manner that the active mixture according to the invention is dissolved in a solvent with high or medium boiling point, preferably in a solvent boiling above 100° C.

Miscible oil preparations can be prepared in such manner that the active mixture according to the invention is dissolved or finely distributed in a suitable solvent, preferably poorly miscible with water, with addition of an emulsifying agent.

Inverted emulsions can be prepared in such manner that an oily solution or suspension of the active mixture according to the invention, either before or during spraying, is emulsified with water in the spraying apparatus.

Aerosols can, for example, be prepared in that the active mixture according to the invention, if necessary in dissolved state, is admixed with a flowable liquid serving as a propellant, such as one of the Freon-type.

Preferably emulsion concentrates, pastes, or wettable powders containing the active agents in relatively high amounts can be applied to advantage for the preparation of aqueous formulations. These [concentrates] are diluted with water to the desired concentration before use. The concentrates should be so prepared as to be storable for prolonged periods of time, and should form, by dilution with water, a sprayable formulation which is homogeneous for sufficiently long time and is sprayable with the conventional spraying devices. The concentrates contain generally 10 to 85% by weight, preferably 25 to 60% by weight, active mixtures. These concentrates are diluted with water preferably to a final active concentration of about 0.001 to 3.00% by weight.

The concentrations of the pesticides according to the invention present in the active mixtures may vary within wide limits. Depending on the desired effect, the method of preparation and the application purpose, these concentrations amount to generally 0.01 to 98% by weight. When the pesticide is applied by the so-called "ultra-low-volume" method, the active mixtures according to the invention contain very low amounts of additives whereby the active content amounts in this case preferably 90 to 98% by weight. In this instance the preparations are spread on the area to be treated preferably from an aircraft, using a spraying device which produces a very fine spray. The active agent contents of the diluted compositions varies generally within 0.01 to 20% by weight, whereas the concentrates can contain generally 20 to 98% by weight of active agents. The active agent content of wettable powders is generally 5 to 80% by weight, preferably 10 to 60% by weight, that of emulsifyiable concentrates is generally 5 to 70% by weight, preferably 10 to 50% by weight, and in powdery compositions is generally 0.5 to 10% by weight, preferably 1 to 5% by weight.

The compositions according to the invention can be applied in the form of sprays, dusts, coating agents as well as, further, soil sprinkling agents, immersion baths. The particular form of the preparation is always selected in accordance with the requirements of the field of application.

In the application of the pesticides according to the invention, they are applied with or without carriers, extenders, diluents and/or auxiliary agents, in ways known per se, to the plants or their parts, the seeds or the ground.

When utilized for the treatment of seeds, the seeds can be coated e.g. under stirring with the active mixture according to the invention and optionally with a carrier. The active mixture according to the invention can, however, also be applied together with surfactants and, if desired, carriers can also be applied onto the seed surface. One can proceed by wetting a mixture of the inorganic salt, herbicidally active organic compound, surfactant and carrier with a small amount of water, and admixing the seeds with the obtained suspension.

In the use of the pesticides according to the invention one can also proceed by introducing a powdery composition containing an active mixture according to the invention, with sand, soil or another powdered solid substance as discussed above and optionally a surfactant into the ground (the furrow) during sowing.

An aqueous spray containing an active mixture according to the invention, optionally together with a surfactant and/or a solid carrier, can also be applied onto the seeds either before, or during or after sowing.

In the use of the pesticides according to the invention or their effective mixtures, in agriculture including horticulture, the effective mixture or a preparation containing same can be applied to the surroundings of the plants, or onto parts (e.g. the leaves) of the plants to be treated, e.g. by spraying, dusting or spreading, or e.g. by sprinkling or flooding, or the compositions can be admixed with the soil prior to sowing, and the seeds can be sown into pre-treated furrows.

The pesticides according to the invention can be used for combatting either monocotyledon or dicotyledon weeds. The treatment can be performed either before or after the emergence of the weeds (pre-emergent and post-emergent treatments, respectively), or, by working into the soil.

The pre-emergent treatment implies that the compositions according to the invention are applied onto the soil before the emergence of weeds, e.g. the soil is sprinkled with an aqueous composition before the weeds emerge from the soil surface. Pre-emergent treatments can also be performed on areas where cultivated plants are already growing, or into which seeds of cultivated plants have already been sown, as long as the weeds have not emerged.

The term post-emergent treatment implies that the herbicidal compositions according to the invention are applied to the area to be treated (e.g. onto the soil or onto the overground part of the weeds) after the emergence of the weeds. This term also implies the treatment according to which the pesticides or their active agent mixtures are applied onto soil wherein cultivated plants are growing; in his instance the active agents exert their herbicidal effects through root absorption. The herbicidal compositions can be applied the environment of the growth area of cultivated plants as well.

The herbicidal compositions according to the invention have been found to be particularly selective on maize, grain, sunflowers, alfalfa, sugar beets, soybeans, potato and rice cultures.

The effective dosage of the pesticides according to the invention depends upon a surprisingly large number of factors, thus e.g. on the type and state of the cultivated plant to be treated, on the other plants growing in their environments, on the type of weeds to be combatted, on the season, on climate conditions and on the mode of application. The effective dosages of pre- and post-emergence treatments may also be different. Accordingly, the optimum dosage levels should be determined empirically in each of the particular cases, but generally 0.1 to 30 kg of active agent per hectare will be sufficient to attain the desired results.

The invention is explained further by the following nonlimiting examples in sections I through VI, whereby examples through the sections are continuously numbered in succession.

I. Preparation of Effective Mixtures

The mixtures are prepared in identical ways, namely in that one or more pesticidally effective organic compounds and one or more of the salts of sodium and/or potassium and bisulphate, bisulphite, dithionite and/or sulphate in the proportions given below are finely powdered by rubbing, mixing and homogenizing.

EXAMPLE 1

24.1 g 2-(tert-butylamino)-4-ethylamino-6-methylthio-1,3,5-triazine and 6.9 g sodiumbisulfatemonohydrate.

EXAMPLE 2

24.1 g 2-(tert-butylamino)-4-ethylamino-6-methylthio-1,3,5-triazine and 13.8 g sodiumbisulfatemonohydrate.

EXAMPLE 3

24.1 g 2-(tert-butylamino)-4-ethylamino-6-methylthio-1,3,5-triazine and 27.6 g sodiumbisulfatemonohydrate.

EXAMPLE 4

24.1 g 2-(tert-butylamino)-4-ethylamino-6-methylthio-1,3,5-triazine and 41.4 g sodiumbisulfatemonohydrate.

EXAMPLE 5

24.1 g 2-(tert-butylamino)-4-ethylamino-6-methylthio-1,3,5-triazine and 69.0 g sodiumbisulfatemonohydrate.

EXAMPLE 6

24.1 g 2-(tert-butylamino)-4-ethylamino-6-methylthio-1,3,5-triazine and 110.4 g sodiumbisulfatemonohydrate.

EXAMPLE 12

22.7 g 2-ethylamino-4-isopropylamino-6-methylthio-1,3,5-triazine and 138.0 g sodiumbisulfatemonohydrate.

TABLE 1

| | Herbicidal Organic Compound | | Inorganic Salt | |
|---|---|---|---|---|
| Example No. | Name | Amount in Weight - % | Name | Amount in Weight - % |
| 13 | 24.1 g 2-(tert-butylamino)-4-ethylamino-6-methylthio-1,3,5-triazine | 63.4 | Sodiumbisulfatemonohydrate | 36.6 |
| 14 | 24.1 g 2-(tert-butylamino)-4-ethylamino-6-methylthio-1,3,5-triazine | 69.0 | Sodiumbisulfite | 31.0 |
| 15 | 24.1 g 2-(tert-butylamino)-4-ethylamino-6-methylthio-1,3,5-triazine | 63.9 | Potassiumbisulfate | 36.1 |
| 16 | 24.1 g 2-(tert-butylamino)-4-ethylamino-6-methylthio-1,3,5-triazine | 62.8 | Sodiumsulfate | 37.2 |
| 17 | 2,4-Di-(isopropylamino)-6-methylthio-1,3,5-triazine | 63.4 | Sodiumbisulfatemonohydrate | 36.6 |
| 18 | 2,4-Di-(isopropylamino)-6-methylthio-1,3,5-triazine | 69.0 | Sodiumbisulfite | 31.0 |
| 19 | 2,4-Di-(isopropylamino)-6-methylthio-1,3,5-triazine | 63.9 | Potassiumbisulfate | 36.1 |
| 20 | 2,4-Di-(isopropylamino)-6-methylthio-1,3,5-triazine | 62.8 | Sodiumsulfate | 37.2 |
| 21 | 2-ethylamino-4-isopropylamino-6-methylthio-1,3,5-triazine | 62.1 | Sodiumbisulfatemonohydrate | 37.9 |
| 22 | 2-ethylamino-4-isopropylamino-6-methylthio-1,3,5-triazine | 68.6 | Sodiumbisulfite | 31.4 |
| 23 | 2-ethylamino-4-isopropylamino-6-methylthio-1,3,5-triazine | 62.4 | Potassiumbisulfate | 37.6 |
| 24 | 2-ethylamino-4-isopropylamino-6-methylthio-1,3,5-triazine | 61.4 | Sodiumsulfate | 38.6 |
| 28 25 | N,N-Dipropyl-2,6-dinitro-4-isopropylaniline | 69.1 | Sodiumbisulfatemonohydrate | 30.9 |
| 29 26 | N,N-Dipropyl-2,6-dinitro-4-isopropylaniline | 74.9 | Sodiumbisulfite | 25.1 |
| 27 | N,N-Dipropyl-2,6-dinitro-4-isopropylaniline | 69.5 | Potassiumbisulfate | 30.5 |
| 28 | N,N-Dipropyl-2,6-dinitro-4-isopropylaniline | 68.5 | Sodiumsulfate | 31.5 |
| 29 | 2-Chloro-4,6-di-(isopropylamino)-1,3,5-triazine | 62.4 | Sodiumbisulfatemonohydrate | 37.6 |
| 31 | 2-Chloro-4,6-di-(isopropylamino)-1,3,5-triazine | 62.7 | Potassiumbisulfate | 37.3 |
| 32 | 2-Chloro-4,6-di-(isopropylamino)-1,3,5-triazine | 61.7 | Sodiumsulfate | 38.3 |
| 33 | N,N-Dipropyl-2,6-dinitro-4-trifluormethylaniline | 70.8 | Sodiumbisulfatemonohydrate | 29.2 |

EXAMPLE 7

24.1 g 2-(tert-butylamino)-4-ethylamino-6-methylthio-1,3,5-triazine and 138.0 g sodiumbisulfatemonohydrate.

EXAMPLE 8

24.1 g 2-(tert-butylamino)-4-ethylamino-6p-methylthio-1,3,5-triazine and 136.0 g potassiumbisulfate.

EXAMPLE 9

24.1 g 2,4-di-(isopropylamino)-6-methylthio-1,3,5-triazine and 136.0 g potassiumbisulfate.

EXAMPLE 10

24.1 g 2,4-di-(isopropylamino)-6-methylthio-1,3,5-triazine and 133.0 g sodiumbisulfatemonohydrate.

EXAMPLE 11

22.7 g 2-ethylamino-4-isopropylamino-6-methylthio-1,3,5-triazine and 136.0 g potassiumbisulfate.

II. Preparation of the Pesticide

EXAMPLE 34

An effective mixture containing 2-(tert-butylamino)-4-ethylamino-6-methylthio-1,3,5-triazine and sodium bisulphate monohydrate in weight ratio of 1:1 as spray powder.

50 parts by weight of a mixture in 1:1 weight ratio of 2-(tert-butylamino)-4-ethylamino-6-methylthio-1,3,5-triazine and sodium bisulphate monohydrate are blended in a homogenizer with 2 parts by weight of an alkylarylpolyglycol ether (Citowett) and 5 parts by weight of powdered sulphite waste liquor, thereafter 45 parts by weight of kaoline are added to the mixture, and [the mixture] is blended until complete homogeneity. Thereafter the mixture is ground in a fine-milling mill to obtain a particle size of at least 20μ. The preparation obtained, containing 50% by weight active agents, can be diluted with water to any desired concentration.

EXAMPLE 35

An effective mixture containing 2-(tert-butylamino)-4-ethylamino-6-methylthio-1,3,5-triazine and sodium bisulphate monohydrate in a weight ratio of 1:1 in the form of an emulsion concentrate.

30 parts by weight of a 1:1 weight-ratio mixture of 2-(tert-butylamino)-4-ethylamino-6-methylthio-1,3,5-triazine and sodium bisulphate monohydrate are admixed with 60 parts by weight of methanol and 10 parts by weight of an emulsifying agent containing calcium dodecylbenzenesulphonate and polyglycolether in a weight ratio of 1:1.

EXAMPLE 36

An effective mixture of 2-ethylamino-4-isopropyl-6-methylthio-1,3,5-triazine and sodium bisulphate monohydrate in a weight ratio of 1.65:1 in the form of a spray liquid.

6.21 g of 2-ethylamino-6-methylthio-4-isopropylamino-1,3,5-triazine and 3.76 g of sodium bisulphate monohydrate are finely powdered in a mortar. The mixture is dissolved in 1000 cm$^3$ of 60% aqueous acetone containing 0.12 g of 40% sodium dioctylsulfosuccinate (Nonit). The solution is used as a spray liquid.

EXAMPLE 37

An effective mixture of 2,4-di-(isopropylamino)-6-methylthio-1,3,5-triazine and potassium bisulphate in the form of a liquid spray.

160 g of Merkazin 50 WP (a commercially available plant protecting agent) whose effective ingredient is 2,4-di-(isopropylamino)-6-methylthio-1,3,5-triazine are suspended with stirring in 1000 cm$^3$ of water. Thereafter 40 g of solid potassium bisulphate are added. Stirring is continued until the potassium bisulphate dissolves completely. The solution is used as a liquid spray.

III. Selectivity Tests (Screening tests)

In the selection of the test plants the sensitivities of the monocotyledons and dicotyledons towards the various herbicidally active organic compounds were taken into account.

Depending upon the herbicidally active organic compounds utilized, different test plants were investigated. As test plants, the following monocotyledons maize (Zea mays), oat (Avena sativa), barley (Hordeum distichon), millet (Panicum miliaceum), green foxtail (Setaria glauca) and barnyard grass (Echinochloa crusgalli) and the following dicotyledons red alfalfa (Trifolium pratense), poppy (Papaver somniferum), sugar beet (Bete vulgaris), tomato (Solanum lycopersicum) and rape (Brassica napus) were included.

Under greenhouse conditions flat, plastic trays with areas of 32×27 cm were filled with quartz sand up to a height of 5 cm. The seeds were placed onto the top of this layer. The seeds were covered with a 1 cm layer of river sand in order to ensure uniform germination. Standard solutions containing 1% or 2% of the herbicidally active organic compound or 1% or 2% of a mixture of the respective herbicidally active organic compound with sodium bisulphate monohydrate, and/or potassium bisulphate, and/or sodium sulphate, and/or sodium bisulphite, and/or sodium dithionite were prepared. These solutions were sprayed in amounts each of 100 cm$^3$ onto 1 m$^2$ areas of the trays in the center of these areas uniformly, these amounts of spray solutions corresponding to dosages of 10 kg/ha or 20 kg/ha. The solutions were sprayed with a hand-operated laboratory spraying device in order to ensure a uniform distribution of the spray on the total area of 1 m$^2$. The trays were put into greenhouses and were observed regularly for 2 weeks.

The herbicidal effect and selectivity was determined on the basis of the ratio of killed seeds to sprouted seeds and by calculating the phytotoxic damage, by counting the germinated plants over a two week period every third day and the phytotoxicity evaluated.

The number of seeds sown in the individual tests varied with their size and circumference.

| | |
|---|---|
| maize (Zea mays) | 10 seeds |
| oat (Avena sativa) | 10 seeds |
| barley (Hordeum distichon) | 10 seeds |
| millet (Panicum miliaceum) | 10 seeds |
| green foxtail (Setaria glauca) | 10 seeds |
| barnyard-grass (Echinochloa crusgalli) | 50 seeds |
| poppy (Papaver somniferum) | 50 seeds |
| sugar beet (Beta vulgaris) | 10 seeds |
| rape (Brassica napus) | 10 seeds |
| tomtao (Solanum lycopersicum) | 50 seeds |

EXAMPLE 38

1 g of an effective mixture containing 62.1% by weight of 2-ethylamino-4-isopropylamino-6-methylthio-1,3,5-triazine (pure substance: Ametryne) and 37.6% by weight of sodium bisulphate monohydrate were dissolved in 100 cm$^3$ of 60% aqueous acetone containing 0.012 g of 40% sodium dioctylsulfosuccinate with 100 cm$^3$ of the same solvent a solution of 1 g of an effective mixture of 62.7% by weight of 2-ethylamino-4-isopropylamino-6-methylthio-1,3,5-triazine and 37.3% by weight of potassium bisulphate is prepared. The reference material was a solution of 1 g of 2-ethylamino-4-isopropylamino-6-methylthio-1,3,5-triazine in 100 cm$^3$ of chloroform containing 0.012 g of 40% sodium dioctylsulfosuccinate. Pre-emergent treatments were performed with the above solutions by applying 10 kg/ha of active agent onto the area to be treated and the effect of the named herbicides containing active mixtures according to the invention and the reference materials was examined.

The results are summarized in the following Table 2.

TABLE 2

| | Killing in % Active Ingredients of Herbicides and Dosages | | |
|---|---|---|---|
| Plants | 2-ethylamino-4-iso-propylamino-6-methylthio-1,3,5-triazine + sodiumbisulfate-monohydrate 10 kg/ha | 2-ethylamino-4-iso-propylamino-6-methylthio-1,3,5-triazine + potassiumbisulfate 10 kg/ha | 2-ethylamino-4-iso-propylamino-6-methylthio-1,3,5-triazine (Control Material) 10 kg/ha |
| Maize (Zea mays) | 0 | 0 | 0 |
| Trifolium pratense | 100 | 100 | 100 |
| Poppy (Papaver somniferum) | 100 | 100 | 100 |
| Rape (Brassica napus) | 80 | 95 | 50 |
| Millet (panicum mileaceum) | 80 | 40 | 10 |
| Green Foxtail (Setaria glauca) | 0 | 0 | 0 |
| Barnyard grass | 0 | 0 | 0 |

From the above Table 2 it will be apparent that, in comparison to the reference material 2-ethylamino-4-isopropylamino-6-methylthio-1,3,5-triazine as the single effective herbicide, the selectivity of the named herbicide according to the invention containing the effective mixture with reference to maize (Zea mays) was unchanged while the herbicidal effect against the herbicide-resistant millet and the damaging rape there is an increase even when the herbicide according to the invention contains only 62 to 63% by weight of the 2-ethylamino-4-isopropylamino-6-methylthio-1,3,5-triazine of the reference material.

EXAMPLE 39

1 g of a mixture containing 63.4% by weight of 2,4-(diisopropylamino)-6-methylthio-1,3,5-triazine and 36.6% by weight of sodium bisulphate monohydrate was dissolved in 100 cm³ of acetone containing 0.012 g of 40% dioctyl-sodium-sulfosuccinate, 1 g of a mixture containing 63.9% by weight of 2,4-(diisopropylamino)-6-methylthio-1,3,5-triazine and 36.1% by weight of potassium bisulphate was dissolved in 100 cm³ of the same solvent. The reference material was 2,4-(diisopropylamino)-6-methylthio-1,3,5-triazine 1 g of (pure substance) in 100 cm³ of chloroform containing 0.012 g of 40% dioctyl-sodium-sulfosuccinate. Pre-emergent treatments were performed with these solutions by applying 10 kg/ha of active agent onto the area to be treated in each of the tests and the effect of the mixture according to the invention and the reference material was determined. The results are summarized in Table 3.

TABLE 3

| | Killing in % Active Ingredients of Herbicides and Dosages | | |
|---|---|---|---|
| Plants | 2,4-(Diisopropyl-amino)-6-methyl-thio-1,3,5-triazine + sodiumbisulfate monohydrate 10 kg/ha | 2,4-(Diisopropyl-amino)-6-methyl-thio-1,3,5-triazine + potassiumbisulfate 10 kg/ha | 2,4-(Diisopropyl-amino)-6-methyl-thio-1,3,5-triazine (Control Material) 10 kg/ha |
| Maize (Zea mays) | 0 | 0 | 0 |
| Trifolium pratense | 100 | 100 | 60 |
| Poppy (Papaver somniferum) | 100 | 100 | 100 |
| Rape (Brassica napus) | 80 | 70 | 20 |
| Millet (Panicum mileaceum) | 70 | 20 | 5 |
| Green Foxtail (Setaria glauca) | 0 | 0 | 0 |
| Barnyard grass (Echinochloa crusgalli) | 5 | 0 | 0 |

It appears from the above Table 3 that by comparison to the reference material containing 2,4-(diisopropylamino)-6-methylthio-1,3,5-triazine as the simple effective herbicide the selectivities of the herbicidal mixtures do not change on maize (Zea mays) with respect to the reference applied in the same dosage, but the mixtures exert 65% stronger herbicidal effect against the herbicide-resistant millet (Panicum miliaceum), and 50 and 60% stronger effect against the dicotyledon rape (Brassica napus), although the mixtures contain only 63 to 64% of the 2,4-(diisopropyl)-6-methylthio-1,3,5-triazine of the reference material.

EXAMPLE 40

Solutions were prepared by dissolving 1 g portions of a herbicidal mixture consisting of 2-(tert-butylamino)-4-ethylamino-6-methylthio-1,3,5-triazine (Terbutryne) and various amounts of sodium bisulphate monohydrate or potassium bisulphate, respectively, in 100 cm³ portions of 60% aqueous acetone containing 0.012 g of 40% sodium dioctylsulfosuccinate. As reference, a solution of 1 g of pure Terbutryne in 100 cm³ of chloroform containing 0.012 g of sodium dioctylsulfosuccinate (Nonit) was used. The solutions were sprayed onto areas of 1 m² each, with the prepared seeded test trays placed into the center of the areas. Accordingly, the active agent in these pre-emergent tests was applied onto the seeds in amounts corresponding to 10 kg/ha. The results are summarized in Table 4.

TABLE 4

| Compound(s) | Herbicidal Composition | | Effective-Agent Dosage | Killrate in % of the Test Plants | | |
|---|---|---|---|---|---|---|
| | Content of 2-(tert-butylamino)-4-ethylamino-6-methylthio-1,3,5-triazine in weight % | Content of Sodiumbisulfate-monohydrate and/or potassium-bisulfate in weight % | | Maize (Zea mays) | Millet (Panicum miliaceum) | Rape (Brassica napus) |
| 2-(tert-butylamino)-4-ethylamino-6-methylthio-1,3,5-triazine + sodiumbisulfate-monohydrate | 77.8 | 22.2 | 10 kg/ha | 0 | 10 | 70 |
| 2-(tert-butylamino)-4-ethylamino-6-methylthio-1,3,5-triazine + sodiumbisulfate-monohydrate | 63.4 | 36.6 | 10 kg/ha | 0 | 10 | 60 |
| 2-(tert-butylamino)-4-ethylamino-6-methylthio-1,3,5-triazine + sodiumbisulfate monohydrate | 46.6 | 53.4 | 10 kg/ha | 0 | 0 | 40 |
| 2-(tert.butylamino)-4-ethylamino-6-methylthio-1,3,5-triazine + sodiumbisulfate-monohydrate | 56.8 | 43.2 | 10 kg/ha | 0 | 10 | 10 |
| 2-(tert-butylamino)-4-ethylamino-6-methylthio-1,3,5-triazine + sodiumbisulfate-monohydrate | 25.1 | 74.9 | 10 kg/ha | 0 | 30 | 20 |
| 2-(tert-butylamino)-4-ethylamino-6-methylthio-1,3,5-triazine + sodiumbisulfate-monohydrate | 17.7 | 82.3 | 10 kg/ha | 0 | 10 | 20 |
| 2-(tert-butylamino)-4-ethylamino-6-methylthio-1,3,5-triazine + sodiumbisulfate-monohydrate | 14.9 | 85.1 | 10 kg/ha | 0 | 40 | 10 |
| 2-(tert-butylamino)-4-ethylamino-6-methylthio-1,3,5-triazine + potassiumbisulfate | 63.9 | 36.1 | 10 kg/ha | 0 | 20 | 70 |
| 2-(tert-butylamino)-4-ethylamino-6-methylthio-1,3,5-triazine (Control Material) | 100 | 0 | 10 kg/ha | 0 | 0 | 0 |

From the above Table 4 it will be apparent that the effective-agent mixture of 2-(tert-butylamino)-4-ethylamino-6-methylthio-1,3,5-triazine and sodium bisulphate monohydrate or potassium bisulphate in the herbicide has a significantly better effect than the reference material and with respect to maize (Zea mays) is as selective as the comparison material. Especially noteworthy is that even the effective-agent mixture of 14.9 weight percent 2-(tert-butylamino)-4-ethylamino-6-methylthio-1,3,5-triazine and 85.1 weight percent sodium bisulphate monohydrate has no phytotoxic effect upon maize. The herbicidal effect against rape (Brassica napus) is, with the herbicides containing effective-agent mixtures with 22.2 weight percent sodium bisulphate monohydrate or 36.6 weight percent potassium bisulphate, especially sharply significantly better than with the reference material.

EXAMPLE 41

In this Example the herbicide, instead of the pre-emergent surface treatment is worked into the soil.

1 g and 2 g, respectively, of a herbicidally effective mixture containing 70.8% by weight of N,N-dipropyl-2,6-dinitro-4-trifluoro-methylaniline and 29.2% by weight of sodium bisulphate monohydrate were dissolved in 100 cm$^3$ of 60% aqueous acetone containing 0.012 g of 40% dioctylsulfosuccinate. As reference, a solution of 1 g of pure N,N-dipropyl-2,6-dinitro-4-trifluoro-methylaniline in 100 cm$^3$ of chloroform containing 0.012 g of 40% sodium dioctylsulfosuccinate was used. The solution was worked into sufficient soil to an effective-agent dosage of 10 or 20 kg/ha. The results of these tests are summarized in the following Table 5.

TABLE 3

|  | Killrate in % Active Ingredients of Herbicides and Dosages | | |
|---|---|---|---|
| Test Plants | N,N-Dipropyl-2,6-dinitro-4-trifluoromethylaniline + sodiumbisulfate-monohydrate 10 kg/ha | N,N-Dipropyl-2,6-dinitro-4-trifluoromethylaniline + sodiumbisulfate-monohydrate 20 kg/ha | N,N-Dipropyl-2,6-dinitro-4-trifluoromethylaniline [control material] 10 kg/ha |
| *Trifolium pratense* | 100 | 100 | 100 |
| Sugarbeet (*Beta vulgaris*) | 10 | 15 | 100 |
| Rape (*Brassica napus*) | 60 | 95 | 80 |
| Millet (*Panicum miliaceum*) | 100 | 100 | 100 |
| Green foxtail (*Setaris glauca*) | 100 | 100 | 100 |
| Barnyard grass (*Echinochloa crus-galli*) | 100 | 100 | 100 |

From the above Table 5 it is apparent that the reference herbicide N,N-dipropyl-2,6-dinitro-4-trifluoromethylaniline as the sole active ingredient killed the sugar beets (Beta vulgaris) while in the same effective-agent dosage or in twice the effective-agent dosage the invention's herbicide containing the given effective-agent mixture was selective as to sugar beets (Beta vulgaris).

IV. Tests on Small Parcels

The tests were performed on brown forest soil (humus content: 2 to 2.5%). The topsoil thickness amounted to 30 to 40 cm. The year before the green crop was harvested, the soil was ploughed in a depth of 20 cm and rolled. The seed bed was prepared (with a diskharrow or cultivator) immediately before sowing. In order to preserve the moisture content of the soil, the soil was treated with a ring-roller, and then the seeds were sown. Pre-emergent spraying was performed with 1000 l/ha amounts of the respective spray solutions (corresponding to 5 kg/ha of active agent). A small-parcel spraying device was used for spraying.

of 2,4-di-(isopropylamino)-6-methylthio-1,3,5-triazine, to the second three parcels a solution of 2-ethylamino-4-isopropyl-6-methylthio-1,3,5-triazine, and to the third, fourth and fifth three parcels a solution each of one of the following effective-agent mixtures (a), (b) or (c) by spraying:

(a) 63% by weight of 2,4-di-(isopropylamino)-6-methylthio-1,3,5-triazine and 37% by weight of sodium bisulphate monohydrate, (b) 64% by weight of 2,4-di-(isopropylamino)-6-methylthio-1,3,5-triazine and 36% by weight of potassium bisulphate, (c) 62% by weight of 2-ethylamino-4-isopropylamino-6-methylthio-1,3,5-triazine and 38% by weight of sodium bisulphate monohydrate.

The data pertaining to the crop yield increasing effects of the herbicidal mixtures according to the invention with respect to the referencescompounds 2,4-di-(isopropylamino)-6-methylthio-1,3,5-triazine and 2-ethylamino-4-isopropylamino-6-methylthio-1,3,5-triazine as single-ingredient reference material, respectively, summarized in the following Table 6. The data are always the average values for the three parcels.

TABLE 6

| Active Ingredients of Herbicides | Effective as dosage in kg/ha | Crop yield in kg/12.5 m² | Crop yield increase in % in relation to the control material (control material = 100%) |
|---|---|---|---|
| 2,4-Di-(isopropylamino)-6-methylthio-1,3,5-triazine + sodiumbisulfate-monohydrate | 5 | 13.5 | 169 |
| 2,4-Di-(isopropylamino)-6-methylthio-1,3,5-triazine + potassiumbisulfate | 5 | 12.0 | 150 |
| 2,4-Di-(isopropylamino)-6-methylthio-1,3,5-triazine [Control material] | 5 | 8.0 | 100 |
| 2-Ethylamino-4-isopropylamino-6-methylthio-1,3,5-triazine + sodiumbisulfate-monohydrate | 5 | 13.3 | 133 |
| 2-Ethylamino-4-isopropylamino-6-methylthio-1,3,5-triazine [reference material] | 5 | 10.0 | 100 |
| Untreated (blind test) | — | 3.8 | — |

EXAMPLE 42

Pink-eye potatoes of "Kisvarda" variety were planted in row distances of 70 cm and stock distances of 50 cm into a parcel with an area of 12.5 m² (=5×2.5 m) in groups of three parcels.

In an effective-agent dosage (consumption amount) each of corresponding to 5 kg/ha in pre-emergent treatment, there was applied to the first 3 parcels, a solution It appears from the data of Table 6 that the herbicidal mixtures of 2,4-di-(isopropylamino)-6-methylthio-1,3,5-triazine or 2-ethylamino-4-isopropylamino-6-methylthio-1,3,5-triazine and sodium bisulphate monohydrate or potassium bisulphate, according to the invention provides a significant increase in crop yield with respect to the reference materials containing 2,4-di-(isopropylamino)-6-methylthio-1,3,5-triazine or 2- ethylamino-4-isopropylamino-6-methylthio-1,3,5-triazine as respective sole effective ingredients used in the following Table 7. The data listed in the Table are the average values observed for the three parcels.

TABLE 7

| Active Ingredients of Herbicides | Effective-Agent Dosage in kg/ha | Green Weight in kg/12.5 m$^2$ | Green Weight Increase in % in Relation to the Control Material (Control Material = 100%) |
| --- | --- | --- | --- |
| 2-(tert-butylamino)-4-ethylamino-6-methylthio-1,3,5-triazine + sodiumbisulfatemonohydrate | 5 | 15.0 | 110 |
| 2-(tert-butylamino)-4-ethylamino-6-methylthio-1,3,5-triazine (control material) | 5 | 14.2 | 100 |
| 2,4-Di-(isopropylamino)-6-methylthio-1,3,5-triazine + sodiumbisulfatemonohydrate | 5 | 15.0 | 125 |
| 2,4-Di-(isopropylamino)-6-methylthio-1,3,5-triazine + potassiumbisulfate | 5 | 13.6 | 115 |
| 2,4-Di-(isopropylamino)-6-methylthio-1,3,5-triazine (control material) | 5 | 12.0 | 100 |
| Untreated (blind test) | — | 4.8 | — | same dosages. When using a mixture of 2,4-di-(isopropylamino)-6-methylthio-1,3,5-triazine and sodium bisulphate monohydrate, particularly high crop yield increases can be attained.

The amounts of cultivated plants and weeds growing in the small parcels were also counted during the test period. These data indicate that the mixture of 2,4-di-(isopropylamino)-6-methylthio-1,3,5-triazine and sodium bisulphate monohydrate exerts a greater herbicidal effect than the 2,4-di-(isopropylamino)-6-methylthio-1,3,5-triazine alone. The herbicidal effects of the mixture 2,4-di-(isopropylamino)-6-methylthio-1,3,5-triazine and potassium bisulphate are essentially identical with those of the 2,4-di-(isopropylamino)-6-methylthio-1,3,5-triazine alone except for Lepidium campestre, which weed was 100% killed by the herbicidal mixture.

EXAMPLE 43

Soybeans (Adepta+Ireg) were shown in row distances of 30 cm into groups of three parcels each with an area of 12.5 m$^2$ (=5×2.5 m). Next day the parcels were treated with spray solutions containing the following active agents for the first three parcels 2-(tert-butylamino)-4-ethylamino-6-methylthio-1,3,5-triazine, for the second three parcels 2,4-di-(isopropylamino)-6-methylthio-1,3,5-triazine and the third, fourth and fifth three parcels with the invention's mixtures (a), (b) and (c):

(a) 65% by weight of 2-(tert-butylamino)-4-ethylamino-6-methylthio-1,3,5-triazine,
35% by weight of sodium bisulphate monohydrate,
(b) 63% by weight of 2,4-di-(isopropylamino)-6-methylthio-1,3,5-triazine,
37% by weight of sodium bisulphate monohydrate,
(c) 64% by weight of 2,4-di-(isopropylamino)-6-methylthio-1,3,5-triazine,
36% by weight of potassium bisulphate.

The data pertaining to the green weight increasing effects of the herbicidal mixtures with respect to the references 2-(tert-butylamino)-4-ethylamino-6-methylthio-1,3,5-triazine or 2,4-di-(isopropylamino)-6-methylthio-1,3,5-triazine, respectively are summarized in the It appears from the above Table 7 that the herbicidal mixtures according to the invention with 2-(tert-butylamino)-4-ethylamino-6-methylthio-1,3,5-triazine or 2,4-di-(isopropylamino)-6-methylthio-1,3,5-triazine and sodium bisulphate monohydrate or potassium sulphate provide a significant increase in green weight with respect to the reference compounds 2-(tert-butylamino)-4-ethylamino-6-methylthio-1,3,5-triazine or 2,4-di-(isopropylamino)-6-methylthio-1,3,5-triazine as sole active ingredients applied in the same dosages. When using a mixture of 2,4-di-(isopropylamino)-6-methylthio-1,3,5-triazine and sodium bisulphate monohydrate, a particularly great increase in green weight can be attained.

The amounts of cultivated plants and weeds growing in the parcels were counted during the test period. These data indicate that the mixture of 2,4-di-(isopropylamino)-6-methylthio-1,3,5-triazine and sodium bisulphate monohydrate exerts greater herbicidal effects than the reference compound 2,4-di-(isopropylamino)-6-methylthio-1,3,5-triazine alone. The herbicidal effects of the mixture 2,4-di-(isopropylamino)-6-methylthio-1,3,5-triazine and potassium bisulphate are essentially identical with those of the reference, but the mixture is significantly more selective than the reference compound 2,4-di-(isopropylamino)-6-methylthio-1,3,5-triazine alone.

EXAMPLE 44

Soybeans were sown in row distances of 30 cm into parcels with an area of 12.5 m$^2$ (=5×2.5 m). Next day the groups of three parcels were each treated with one of the following spray solutions:

The first three parcels with a solution of 2-ethylamino-4-isopropylamino-6-methylthio-1,3,5-triazine and the other three parcels with a solution of 63% by weight of 2-ethylamino-4-isopropylamino-6-methylthio-1,3,5-triazine and 37% by weight of sodium bisulphate monohydrate.

The seed-crop increasing effect of the use of the effective mixture of the invention's herbicide with respect to the reference 2-ethylamino-4-isopropylamino-6-methylthio-1,3,5-triazine as the sole effective agent was determined and the data are summarized in the following Table 8. The data listed in the Table are the average values on three parcels.

TABLE 8

| Active Ingredients of Herbicides | Effective-Agent Dosage in kg/ha | Seed Crop in g/12.5 m² | Increase in Seed Crop in % in Relation to the Control Material (Control Material = 100%) |
|---|---|---|---|
| 2-ethylamino-4-isopropylamino-6-methylthio-1,3,5-triazine + sodiumbisulfatemonohydrate | 5 | 1 070 | 123 |
| 2-ethylamino-4-isopropylamino-6-methylthio-1,3,5-triazine (control material) | 5 | 868 | 100 |

As is apparent from the above Table 8 the effective agent mixture of 2-ethylamino-4-isopropylamino-6-methylthio-1,3,5-triazine and sodium bisulphate monohydrate of the invention's herbicide provides a significant increase in seed-crop yield with respect to the reference compound 2-ethylamino-4-isopropylamino-6-methylthio-1,3,5-triazine as the sole effective ingredient used in the same dosage, although the effective-agent mixture of the invention's herbicide contains 37 weight percent less of 2-ethylamino-4-isopropylamino-6-methylthio-1,3,5-triazine.

EXAMPLE 45

Treatment of Potatoes

Pink-eye potatoes (variety: Keszthely) were planted into parcels with areas of 15 m² (=3×5 m) in row distances of 60 cm and stock distances of 30 cm. The individual parcels were each treated prior to plant emergence with one of the following compositions:

Herbicide Q: 6 g 50 WT % of 2-tert-butylamino-4-ethylamino-6-methylthio-1,3,5-triazine containing wettable powder.

Herbicide R: 3.84 g of 50 WT % of 2-tert-butylamino-4-ethylamino-6-methylthio-1,3,5-triazine containing wettable powder and 1.07 g of sodium bisulfate monohydrate (weight ratio of 2-tert-butylamino-4--ethylamino-6-methylthio-1,3,5-triazine: sodium bisulfate monohydrate 1:0.56).

Herbicide S: 6 g of commercial wettable powder containing 50 WT % 2,4-di-(isopropylamino)-6-methylthio-1,3,5-triazine.

Composition T: 3.84 g of commercial wettable powder containing 50 WT % 2,4-di-(isopropylamino)-6-methylthio-1,3,5-triazine and 1.07 g of sodium bisulfate monohydrate (weight ratio of 2,4-di-(isopropylamino)-6-methylthio-1,3,5-triazine: sodium bisulfate monohydrate = 1:0.56).

The plants were observed 2 months after planting. The results are summarized in the following Table 9.

TABLE 9

| Herbicide | Dosage Expressed as Pure Active Agent in kg/ha | Weediness in % |
|---|---|---|
| R | 2 | 4.37 |
| Q (Control Material) Untreated | 2 | 7.50 |
| Blind Test | — | 72.00 |
| T | 2 | 9.75 |
| S (Control Material) Untreated | 2 | 7.63 |

TABLE 9-continued

| Herbicide | Dosage Expressed as Pure Active Agent in kg/ha | Weediness in % |
|---|---|---|
| Blind Test | — | 52.1 |

Reference herbicide Q (50 WT % of 2-tert-butylamino-4-ethylamino-6-methylthio-1,3,5-triazine containing wettable powder), reduces the weediness of the parcel significantly (by about 90%) in relation to the untreated blind test parcel; herbicide R a composition according to the invention containing 50 WT % of 2-tert-butylamino-4-ethylamino-6-methylthio-1,3,5-triazine containing wettable powder and sodium bisulfate monohydrate, exerts a still stronger herbicidal effect. Using the weediness of the parcel treated with the reference herbicide Q as the base of 100%, the reduction in weediness achieved by the invention herbicide amounted to about 42%. Furthermore 36% of 2-tert-butylamino-4-ethylamino-6-methylthio-1,3,5-triazine effective agent was spared.

Herbicide S (commercial wettable powder containing 50 WT % 2,4-di-(isopropylamino)-6-methylthio-1,3,5-triazine), used as reference, reduces the weediness of the parcel by about 85% in relation to the untreated blind test parcel. The herbicidal effect of herbicide R, a composition according to the invention containing commercial wettable powder containing 50 WT % 2,4-di-(isopropylamino)-6-methylthio-1,3,5-triazine along with sodium bisulfate monohydrate, is practically the same as that of the reference although this effect is attained with about 36% less 2,4-di-(isopropylamino)-6-methylthio-1,3,5-triazine effective agent.

The potatoes were harvested after maturation and the weights were determined. The yields are summarized in the following Table 10.

TABLE 10

| Herbicide | Dosage Expressed as Pure Active Agent in kg/ha | Crop Yield in % Control Material = 100% |
|---|---|---|
| R | 2 | 124.8 |
| Q (Control Material) Untreated | 2 | 100 |
| Blind Test | — | 54.7 |
| T | 2 | 160.0 |
| S (Control Material) Untreated | 2 | 100.0 |
| Blind Test | — | 75.0 |

The data of Table 10 show that herbicides R and T according to the invention provide significant increases in crop yield in relation to the references herbicides Q and S, respectively. Invention herbicides T containing 2,4-di-(isopropylamino)-6-methylthio-1,3,5-triazine and sodium bisulfate monohydrate in a weight ratio of 1:0.56 are particularly advantageous. This herbicide T gives a 60% increase in crop yield although the 2,4-di-(isopropylamino)-6-methylthio-1,3,5-triazine content is 33% lower than in reference herbicide S.

A comparison of these results with those obtained in the tests described in Example 79 under Point IV (performed one year earlier under different meteorological conditions and on different soil) shows that the crop yields are in surprising harmony with each other. This indicates the reproducibility of the agricultural process involving the herbicides according to the invention.

EXAMPLE 46

Treatment of soybeans

Soybeans ("Ireg") were sown into parcels with areas of 17.5 m$^2$ (=3.5×5 m) in row distances of 70 cm. Prior to sowing the parcels were each treated with one of the following herbicides:

Herbicide U: (reference) 4.9 cm$^3$ (4.45 g.) of commercial plant protective emulsion concentrate containing as effective agent 26 wt.% N,N-dipropyl-2,6-dinitro-4-trifluoromethylaniline.

Herbicide V: 3.8 cm$^3$ (3.45 g.) of commercial plant protective emulsion concentrate containing as effective agent 26 wt.% N,N-dipropyl-2,6-dinitro-4-trifluoromethylaniline and 0.36 g. of sodium bisulfate monohydrate (weight ratio of N,N-dipropyl-2,6-dinitro-4-trifluoromethylaniline: sodium bisulfate monohydrate = 1:0.44)

Herbicide W: (reference) 11.2 cm$^3$ (10.8 g.) of commercial plant protective emulsion concentrate containing as effective agent 20 wt.% N-(n-butyl)-N-ethyl-2,6-dinitro-4-trifluoromethylaniline Herbicide X: 7.7 cm$^3$ (7.45 g.) of commercial plant protective emulsion concentrate containing as effective agent 20 wt.% N-(n-butyl)-N-ethyl-2,6-dinitro-4-trifluoromethylaniline and 0.7 g. of sodium bisulfate monohydrate (weight ratio N-(n-butyl)-N-ethyl)-2,6-dinitro-4-trifluoromethylaniline: sodium bisulfate monohydrate —1:0.47)

Herbicide Y: (reference) 4.2 cm$^3$ (4.63 g.) of commercial plant protective emulsion concentrate containing as effective agent 70 wt.% of N,N-dipropyl-2,6-dinitro-4-isopropylaniline Herbicide Z: 2.5 cm$^3$ (2.75 g.) of commercial plant protective emulsion concentrate containing as effective agent 70 wt.% of N,N-dipropyl-2,6-dinitro-4-isopropylaniline and 0.91 g. of sodium bisulfate monohydrate (weight ratio of N,N-dipropyl-2,6-dinitro-4-isopropylaniline: sodium bisulfate monohydrate 1:0.48).

The results observed 2 months after sowing are summarized in the following Table 11.

TABLE 11

| Herbicide | Dosage Expressed as Pure Active Agent in kg/ha | Weediness in % |
|---|---|---|
| V | 0.67 | 0.8 |
| U (Control Material) | 0.67 | 0.5 |
| X | 1.25 | 0.1 |
| W (Control Material) | 1.24 | + |

TABLE 11-continued

| Herbicide | Dosage Expressed as Pure Active Agent in kg/ha | Weediness in % |
|---|---|---|
| Z | 2.1 | 2.4 |
| Y | 1.86 | 5.8 |
| Untreated Blind Test | — | 30.1 |

Key: + Weediness was too small to be expressed in percentages.

From the foregoing Table 11 it is apparent that commercial plant protective emulsion concentrate containing as effective agent 26 wt.% N,N-dipropyl-2,6-dinitro-4-trifluoromethylaniline (Herbicide U), used as reference, reduces the weediness of the parcel significantly, indeed by about 98%, in relation to the untreated blind test parcel. Herbicide V, a composition according to the invention containing commercial plant protective emulsion concentrate containing as effective agent 26 wt.% N,N-dipropyl-2,6-dinitro-4-trifluoromethylaniline sodium bisulfate monohydrate, exerts practically the same weed killing effect as the reference at the same active ingredient dosage but Herbicide V uses about 23% less N,N-dipropyl-2,6-dinitro-4-trifluoromethylaniline.

Commercial plant protective emulsion concentrate containing as effective agent 20 wt.% N-(n-butyl)-N-ethyl-2,6- dinitro-4-trifluorometylaniline (Herbicide W), used as reference, kills practically all weeds. Use of Herbicide X, a composition according to the invention containing commercial plant protective emulsion concentrate containing as effective agent 20 wt.% N-(n-butyl)-N-ethyl-2,6-dinitro-4-trifluoromethylaniline and sodium bisulfate monohydrate, gives practically the same weed killing effect as the reference Herbicide W when used in practically the same dosage, but with a saving of about 31% of the effective agent N-(n-butyl)-N-ethyl-2,6-dinitro-4-trifluoromethylaniline.

Commercial plant protective emulsion concentrate containing as effective agent 70 wt.% of N,N-dipropyl-2,6-dinitro-4-isopropylaniline (Herbicide Y), used as reference, reduces the weediness of the parcel significantly by about 81% in relation to the untreated parcel. Herbicide Z, a composition according to the invention containing commercial plant protective emulsion concentrate containing as effective agent 70 wt.% of N,N-dipropyl-2,6-dinitro-4-isopropylaniline and sodium bisulfate monohydrate, exerts 59% better weed killing effect than the reference Herbicide Y when used in only about 13% higher dosage and enables a saving of about 41% of the effective agent N,N-dipropyl-2,6-dinitro-4-isopropylaniline.

Moreover the plants treated with the herbicides according to the invention are stronger, greener and healthier in appearance than the plants treated with the reference compositions.

VI. Tests Performed on Medium-Size Parcels

Parcels of sandy loam soil, containing 2 to 3% of organic substances and sown with wild pea were harvested at the end of May and were prepared for silo corn by the usual agrarian treatment as follows:

the stubble was dragged by disk harrow, plowing to a depth of 20 cm, and levelling with two harrowings using a combination of disk and spike harrows.

The aqueous solutions were sprayed prior to or after plant emergence in amounts of 800 l/ha, using a John Deere type spraying device.

In the following examples the named combinations of known plant protecting agents or the invention's plant protecting agents were worked into the soil in parcels of 144 m² (=9×16 m) for the pre-emergent application and thereafter silage corn was sown into the soil with a six-row JD type sowing machine.

EXAMPLE 47

Parcels of 144 m² in area were treated with the invention's plant protective agents listed in Table 21 or combinations of known plant protective agents (reference herbicides) in pre-emergent technique.

The average weediness values of the individual parcels and the average heights of the plants are listed in the following Table 12.

crop yields of the individual parcels are given in the following Table 13.

TABLE 13

| Parcel No. | Average Crop Yield in % (control herbicide = 100%) |
|---|---|
| C/2 | 113 |
| C/3 | 127 |
| C/4 | 125 |
| C/1 (with the control herbicide treated parcel) | 100 |
| C/5 (blind test parcel) [untreated] | 102 |

From the above Table 13 it is apparent that the parcels treated with the herbicidal compositions according to the invention provide better crop yields that the

TABLE 12

| Parcel No. | Herbicide | Dosage in Kg/ha | Average Weediness in % | Average Height of the Plants in % (control parcel = 100%) |
|---|---|---|---|---|
| C/2 | As active ingredient 2-Chloro-4-ethylamino-6-isopropylamino-1,3,5-triazine containing suitable plant protection medium + as active ingredient N-Isopropyl-α-chloroacetanilide containing suitable plant protection medium + Sodiumbisulfate-monohydrate | 2 + 4 + 5 | 0.7 | 120 |
| C/3 | As active ingredient 2-Chloro-4-ethylamino-6-isopropylamino-1,3,5-triazine containing suitable plant protection medium + as active ingredient N-Isopropyl-α-chloroacetanilide containing suitable plant protection medium + Potassiumbisulfate | 2 + 4 + 5 | 0.9 | 125 |
| C/4 | As active ingredient 2-Chloro-4-ethylamino-6-isopropylamino-1,3,5-triazine containing suitable plant protection medium + as active ingredient N-Isopropyl-α-chloroacetanilide containing suitable plant protection medium + Sodiumsulfate | 2 + 4 + 5 | 0.3 | 118 |
| C/1 (with the control herbicide treated parcel) | As active ingredient 2-Chloro-4-ethylamino-6-isopropylamino-1,3,5-triazine containing suitable plant protection medium (Gesaprin) + as active ingredient N-Isopropyl-α-chloroacetanilide containing suitable plant protection medium (Ramrod) [control herbicide] | 3 + 6 | 0.5 | 100 |
| C/5 (blind test parcel) [untreated] | — | | 6.8 | 89 |

From the above Table 12 it is apparent that the parcels treated with herbicidal compositions according to the invention show significantly less weed growth than the untreated blind-test parcels. The herbicidal effects of the invention's herbicide are in one case slightly better and in the other cases slightly less than those of the reference. The average height of the plants was, however, substantially greater in each case of the use of the invention's herbicide than with the use of the reference herbicide and the blind tests.

At the end of the growth season the plant heights observed in the corn treated with the herbicides according to the invention exceed by 18 to 25% those treated with the reference herbicides and even during the growth season it can be observed that upon the treatment with the herbicides according to the invention the germination of the seeds was quicker and more strongly developed. The plants were during the entire growth period of a deeper and healthier green than those treated with the reference herbicides, although the latter contained more of the herbicidally active organic agents (2-chloro-4-ethylamino-6-isopropylamino-1,3,5-triazine and N-isopropyl-α-chloroacetanilide). None of the latter was in any case phytotoxic toward the maize.

At the end of the growth season the crop was harvested with a E-280 type silage combine-harvester. The reference herbicide treated parcels and the blind test.

By the use of the invention's herbicides by comparison with the use of the reference herbicides there was achieved an increase in the crop yield of 13 to 27%. This 13 to 27% increase in crop yield was achieved with a saving of about 33% of the herbicidally effective organic agents. A comparison of these results with those observed in the tests described in Example 82 of point V, performed at a different place, on different soil, indicates that the increase in crop yields attained with the invention's herbicides are in substantial agreement. This is a support for the reproducibility of the use of the invention's herbicides or, put otherwise, the effects attainable with the invention's herbicides.

We claim:

1. A herbicidal composition for application to a plant site to promote the growth of potatoes or soybeans and limit the growth of weeds, said composition consisting essentially of a carrier and an amount of 0.01 to 98 by percent of a herbicidally effective component consisting essentially of a mixture of an organic herbicide selected from the group which consists of 2-ethylamino-4-isopropylamino-6-methylthio-1,3,5-triazine; 2,4-di-(isopropylamino)-6-methylthio-1,3,5-triazine; and 2-tert-butylamino-4-ethylamino-6-methylthio-1,3,5-triazine, and at least one inorganic compound selected from the group which consists of sodium bisulfate and potassium bisulfate, the weight ratio of the inorganic compound to the organic compound being substantially 0.1:1 to 15:1.

2. The composition defined in claim 1 wherein said inorganic compound is sodium bisulfate.

3. The composition defined in claim 1 wherein said inorganic compound is potassium bisulfate.

4. The composition defined in claim 1 wherein said organic compound is 2-tert-butylamino-4-ethylamino-6-methylthio-1,3,5-triazine and the inorganic compound is sodium bisulfate.

5. A method of promoting the growth of potatoes or soybean plants in a plant site and controlling the growth of weeds at said site, said method comprising the step of applying to said site 0.1 to 30 kg/hectare of a herbicidal composition containing an inorganic compound and an organic herbicide in a weight ratio of 0.1:1 to 15:1, said inorganic compound being selected from the group which consists of sodium bisulfate and potassium bisulfate and said organic compound being selected from the group which consists of:

2-ethylamino-4-isopropyl-amino-6-methylthio-1,3,5-triazine;
2,4-di-(isopropylamino)-6-methylthio-1,3,5-triazine; and
2-tert-butylamino-4-ethylamino-6-methylthio-1,3,5-triazine.

6. The method defined in claim 5 wherein said organic compound is 2-tert-butylamino-4-ethylamino-6-methylthio-1,3,5-triazine and said inorganic compound is sodium bisulfate.

7. The method defined in claim 5 wherein said composition contains 0.01 to 98% by weight of the mixture of said inorganic and organic compounds, the balance at least one carrier.

8. The method defined in claim 7 wherein said composition is sprayed onto said site as a pre-emergent spray.

9. The method defined in claim 7 wherein said composition is sprayed onto said site as a postemergent spray.

10. A composition applicable to a plant site in an amount of 0.1 to 30 kg/hectare for promoting the growth of potatoes and restricting the growth of weeds, said composition consisting of an inorganic compound and a herbicidally effective organic compound in a synergistic weight ratio of 0.1:1 to 15:1, said inorganic compound being selected from the group which consists of sodium bisulfate and potassium bisulfate, said organic compound being a triazine selected from the group which consists of:

2-ethylamino-4-isopropyl-amino-6-methylthio-1,3,5-triazine;
2,4-di(isopropylamino)-6-methylthio-1,3,5-triazine; and
2-tert-butylamino-4-ethylamino-6-methylthio-1,3,5-triazine.

11. A method of controlling weeds on a potato growth site which comprises applying 0.1 to 30 kg/hectare of the composition defined in claim 10 to said site.

12. The composition according to claim 1 wherein the ratio of the inorganic compound to organic herbicide is substantially 0.44:1 to 1:1.

13. The method according to claim 5 wherein the ratio of the inorganic compound to the organic herbicide is substantially 0.44:1 to 1:1.

14. Composition according to claim 10 wherein the ratio of inorganic compound to the organic herbicide is substantially 0.44:1 to 1:1.

* * * * *